US011241545B2

(12) United States Patent
Thorley et al.

(10) Patent No.: US 11,241,545 B2

(45) Date of Patent: Feb. 8, 2022

(54) RETRACTABLE SYRINGE WITH IMPROVED DELIVERY EFFICIENCY AND LOCKING SYSTEM

(71) Applicant: UNL Holdings LLC, New York, NY (US)

(72) Inventors: Craig Stephen Thorley, Largs (AU); Joseph Hermes Kaal, Raworth (AU); Richard Sokolov, Earlwood (AU); Ernesto Hueso, Randwick (AU); Huw Wallis, Gladesville (AU); Scott Chad, Erskineville (AU); Christopher Dunn, Spring Farm (AU)

(73) Assignee: UNL HOLDINGS LLC, New York, NY (US)

( * ) Notice: Subject to any disclaimer, the term of this patent is extended or adjusted under 35 U.S.C. 154(b) by 68 days.

(21) Appl. No.: 16/121,321

(22) Filed: Sep. 4, 2018

(65) Prior Publication Data

US 2019/0076603 A1 Mar. 14, 2019

Related U.S. Application Data

(62) Division of application No. 14/577,262, filed on Dec. 19, 2014, now Pat. No. 10,092,708, which is a (Continued)

(51) Int. Cl.

*A61M 5/32* (2006.01)
*A61M 5/315* (2006.01)
(Continued)

(52) U.S. Cl.

CPC ........ *A61M 5/322* (2013.01); *A61M 5/31511* (2013.01); *A61M 5/50* (2013.01);
(Continued)

(58) Field of Classification Search

CPC .. A61M 5/322; A61M 5/3232; A61M 5/3234; A61M 2005/3231;
(Continued)

(56) References Cited

U.S. PATENT DOCUMENTS 4,950,241 A * 8/1990 Ranford ................ A61M 5/322 604/110
4,994,034 A 2/1991 Botich
(Continued)

FOREIGN PATENT DOCUMENTS

EP 1184048 A 3/2002
EP 1514566 B 8/2008
(Continued)

OTHER PUBLICATIONS

Australian Patent Office, Patent Examination Report 1 for AU Application No. 2014218378, 5 pgs (dated Jun. 7, 2015).
(Continued)

*Primary Examiner* — Nilay J Shah

(74) *Attorney, Agent, or Firm* — Hamilton, Brook, Smith & Reynolds, P.C.

(57) ABSTRACT

A plunger, a needle assembly and a retractable syringe comprising same are provided. The plunger comprises a plunger member and a plunger outer having a lock spring that prevents or impedes movement of the plunger member after needle retraction. The plunger further comprises another locking member for engaging the barrel to prevent or impede further movement of the plunger outer after delivery of fluid contents. The plunger member has a plunger seal which engages a retractable needle of the needle assembly for retraction. The retractable needle comprises a cannula and needle body with a plurality of fluid channels that co-operate with a fluid conduit of the plunger seal to efficiently direct fluid to the cannula. A needle
(Continued)

312 315 315 312 312 310 300 311 313 314 320B 320A 321A 321B retainer comprises a plurality of barbed arms releasably coupled to the needle body, whereby an ejector with tabs facilitates release of the retractable needle from the needle retainer to allow compressed spring-driven retraction.

18 Claims, 12 Drawing Sheets

Related U.S. Application Data division of application No. 13/516,692, filed as application No. PCT/AU2010/001677 on Dec. 10, 2010, now Pat. No. 8,945,048.

(60) Provisional application No. 61/289,259, filed on Dec. 22, 2009.

(51) Int. Cl.
*A61M 5/50* (2006.01)
*B32B 37/14* (2006.01)
*B32B 37/18* (2006.01)

(52) U.S. Cl.
CPC ............ *B32B 37/142* (2013.01); *B32B 37/18* (2013.01); *A61M 5/3234* (2013.01); *A61M 2005/323* (2013.01); *A61M 2005/3231* (2013.01); *A61M 2205/19* (2013.01); *A61M 2207/00* (2013.01); *Y10T 29/49826* (2015.01)

(58) Field of Classification Search
CPC .... A61M 2005/323; A61M 2005/3235; A61M 2005/3238; A61M 2005/3236; A61M 2005/3241; A61M 5/001; A61M 2207/00; A61M 2207/01; Y10T 29/49826
See application file for complete search history.

(56) References Cited

U.S. PATENT DOCUMENTS 5,114,404 A 5/1992 Paxton et al.
5,211,628 A 5/1993 Marshall
5,308,329 A 5/1994 Mazur et al.
5,423,758 A 6/1995 Shaw
5,800,395 A 9/1998 Botich
6,066,115 A 5/2000 Lai
6,083,199 A 7/2000 Thorley
6,086,568 A 7/2000 Caizza
6,287,279 B1 9/2001 Siekmann
6,432,087 B1 8/2002 Hoeck
6,945,960 B2 9/2005 Barker
6,966,898 B1 11/2005 Pouget et al.
7,390,312 B2 6/2008 Barrelle
7,468,054 B2 12/2008 Crawford et al.
7,500,967 B2 3/2009 Thorley
7,645,265 B2 1/2010 Stamp
7,935,087 B2 5/2011 Judd
8,002,745 B2 8/2011 Kaal
8,021,333 B2 9/2011 Kaal
8,052,654 B2 11/2011 Kaal
8,114,050 B2 2/2012 Kaal
8,167,837 B2 5/2012 Judd
8,361,035 B2 1/2013 Thorley
8,617,122 B2 12/2013 Judd
8,945,048 B2 2/2015 Thorley
10,092,708 B2 10/2018 Thorley
2002/0169421 A1 11/2002 McWethy
2003/0158525 A1 8/2003 Thorley
2003/0212362 A1 11/2003 Roser
2005/0080382 A1 4/2005 Hsieh et al.
2006/0069348 A1 3/2006 Parker et al.
2006/0235354 A1 * 10/2006 Kaal .................. A61M 5/3234 604/110
2008/0021389 A1 1/2008 Runfola
2008/0097337 A1 4/2008 Judd
2008/0208143 A1 8/2008 Kaal
2008/0228143 A1 9/2008 Stamp
2008/0234635 A1 9/2008 Shue et al.
2008/0255513 A1 10/2008 Kaal
2009/0093759 A1 * 4/2009 Judd .................. A61M 5/3234 604/110
2009/0131879 A1 5/2009 Lu
2009/0221962 A1 9/2009 Kaal
2010/0010450 A1 1/2010 Runfola
2011/0015572 A1 1/2011 Thorley
2011/0190699 A1 8/2011 Judd
2012/0130317 A1 5/2012 Thorley
2013/0060191 A1 3/2013 Thorley
2013/0060202 A1 3/2013 Thorley
2013/0060231 A1 3/2013 Adlon
2013/0079716 A1 3/2013 Thorley
2013/0102973 A1 4/2013 Thorley
2013/0338602 A1 12/2013 Thorley
2015/0141936 A1 5/2015 Thorley

FOREIGN PATENT DOCUMENTS

GB 2341804 B 2/2003
WO WO 2005/072801 A1 8/2005
WO WO 2006/044390 A2 4/2006
WO WO 2006/108243 A2 10/2006
WO WO-2006108243 A2 * 10/2006 .......... A61M 5/3234
WO WO 2009/003234 A1 1/2009

OTHER PUBLICATIONS

European Patent Office, Supplementary European Search Report for European Patent Application No. 10838400.9, 7 pgs (dated Sep. 3, 2013).
European Patent Office, European Extended Search Report for EP Application No. 15162052.3, 7 pgs (dated Jul. 23, 2015).
Final Office Action for U.S. Appl. No. 14/577,262, dated Dec. 22, 2017.
Non-Final Office Action for U.S. Appl. No. 14/577,262, dated May 24, 2017.
Notice of Allowance for U.S. Appl. No. 14/577,262, dated Jun. 1, 2018.

* cited by examiner

RETRACTABLE SYRINGE WITH IMPROVED DELIVERY EFFICIENCY AND LOCKING SYSTEM

RELATED APPLICATION(S)

This application is a divisional of U.S. application Ser. No. 14/577,262, filed Dec. 19, 2014, which is a divisional of U.S. application Ser. No. 13/516,692, filed Nov. 20, 2012, now U.S. Pat. No. 8,945,048, issued Feb. 3, 2015, which is the U.S. National Stage Application of International Application No. PCT/AU2010/001677, filed on Dec. 10, 2010 and designating the United States, published in English, which claims the benefit of U.S. Provisional Application No. 61/289,259, filed on Dec. 22, 2009. The entire teachings of the above applications are incorporated herein by reference.

FIELD

This invention relates to syringes. More particularly, this invention relates to a retractable syringe that includes at least one lock to prevent re-use of the syringe and/or needle stick injury and/or provides more efficient fluid delivery.

BACKGROUND

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

Furthermore, health professionals may be exposed to used syringes which can lead to inadvertent needle stick injuries and possible exposure to infective pathogens or other contaminants.

In response to this problem, retractable syringes have been developed with the aim of preventing syringe re-use and/or needle stick injury by used syringes.

SUMMARY

While retractable syringes have been developed with the aim of preventing syringe re-use and/or needle stick injury, there is still a need to improve the safety and efficiency of retractable syringes while keeping manufacturing costs to a minimum, particularly for mass produced retractable syringes.

A preferred object of the invention is to provide a user friendly and safe retractable syringe while keeping manufacturing costs to a minimum, thereby facilitating mass production and distribution of retractable syringes.

Another preferred object of the invention is to provide a retractable syringe which efficiently delivers fluid contents, thereby minimizing wastage of fluid contents.

Yet another preferred object of the invention is to provide one or more locking systems to prevent or at least minimize syringe re-use and/or needle stick injury.

In a first aspect, the invention provides a plunger for a retractable syringe that comprises a barrel and a retractable needle, said plunger comprising a plunger member, a plunger outer and one or more locking members.

Suitably, a first said locking member in use prevents or impedes movement of said plunger member relative to said plunger outer and/or said barrel after needle retraction.

In one embodiment, the first locking member is a lock spring mounted to the plunger outer.

In another embodiment, the plunger comprises a second locking member. Preferably, the plunger outer comprises the second locking member which is capable of engaging the barrel. Suitably, the second locking member is capable of engaging the barrel. at the end of injection of fluid contents to thereby prevent or impede further movement of the plunger outer relative to the barrel.

Preferably, the plunger further comprises a biasing member, wherein the plunger member and plunger outer co-operate to releasably maintain said biasing member in an initially energized state.

Suitably, retraction of said retractable needle is facilitated by a release of energy from said biasing member.

Non-limiting examples of biasing members include a spring, elastic or other device for storing releasable energy.

Preferably, the biasing member is a spring which is initially compressed.

In the context of the initially energized biasing member, or the initially compressed spring, it will be appreciated that energizing of the basing member or compression of the spring is performed during manufacture of the plunger or retractable syringe (i.e before supply to, or purchase or operation by, the user).

In one embodiment, the plunger further comprises a retractable needle-engaging member.

Preferably, the plunger further comprises a plunger seal.

In one embodiment, the plunger seal is mounted to the plunger member.

In one preferred embodiment, the plunger seal comprises said retractable needle-engaging member.

In a particularly preferred embodiment, the plunger seal further comprises one or more fluid conduits.

The plunger may further comprise a control rod. Preferably, the control rod is releasably connected to the plunger member. More preferably, the control rod is frangibly connected to the plunger member.

In a second aspect, the invention provides a retractable syringe comprising a barrel; a retractable needle; and the plunger of the first aspect.

In a third aspect, the invention provides a needle assembly comprising a retractable needle that comprises a cannula and a needle body comprising one or more conduits that in use direct fluid to said cannula.

Preferably, in use the one or more conduits co-operate with one or more fluid channels of a plunger seal to direct fluid to said cannula.

Suitably, said needle body is engageable by a needle-engaging member of a plunger.

Preferably, the needle assembly further comprises a needle retainer releasably coupled to said needle body. In a preferred form, the needle retainer comprises a plurality of barbed arms that in use are releasably coupled to said needle body. the needle retainer may comprise a plurality of centering bosses that facilitate self-centering of the needle retainer during syringe assembly. The needle retainer may comprise a plurality of guide channels which facilitate or guide the flow of glue or adhesive for adhering the needle retainer to the barrel during syringe assembly.

Suitably, the needle assembly further comprises an ejector.

Suitably, the ejector facilitates release of the retractable needle from the retainer to facilitate retraction of said retractable needle when engaged by said plunger.

In a preferred embodiment the ejector comprises a plurality of tabs that releasably engage said retractable needle.

Preferably, said tabs provide an acceptable or desired level of retraction activation force for disengaging from the retractable needle.

Preferably, the needle assembly further comprises a needle seal.

In a fourth aspect, the invention provides a retractable syringe comprising a barrel and the needle assembly of the third aspect mounted thereto.

Preferably, said barrel further comprises a collar having one or more releasing members that facilitate release of said controlling member from said plunger outer.

Preferably, said syringe comprises a lock formed between said barrel or said collar and said plunger outer after injection of fluid contents of said syringe.

Suitably, the syringe according to the aforementioned aspects is a prefilled syringe.

In this context, "prefilled" means that the retractable syringe contains deliverable fluid contents before supply to, or purchase or operation by, the user. Accordingly, a prefilled syringe obviates the step of the user filling the syringe with fluid contents.

According to the aforementioned aspects, typically, although not exclusively, the barrel is formed of glass.

In a fifth aspect, the invention provides a method of making a retractable syringe by assembling a plunger, needle assembly and/or barrel according to any of the aforementioned aspects.

Suitably, the method includes the step of inserting a needle retainer into a barrel of the retractable syringe, the needle retainer comprising a plurality of centering bosses that facilitate self-centering of the needle retainer in the barrel.

Preferably, the method includes the step of adhering the needle retainer to the barrel by providing a flow of adhesive through guide channels of said needle retainer.

In a particularly preferred embodiment, the method of making the retractable syringe includes the sequential steps of:

(i) mounting a needle assembly as hereinbefore described to a syringe barrel;

(ii) filling the barrel with fluid contents;

(iii) inserting a plunger seal into the barrel; and (iv) coupling a plunger to the plunger seal.

Preferably, a collar comprising one or more releasing members is adhered to the barrel prior to step (ii).

In a sixth aspect, the invention provides a method of operating a syringe according to any of the aforementioned aspects.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

The teachings of all patents, published applications and references cited herein are incorporated by reference in their entirety.

Figure 1:
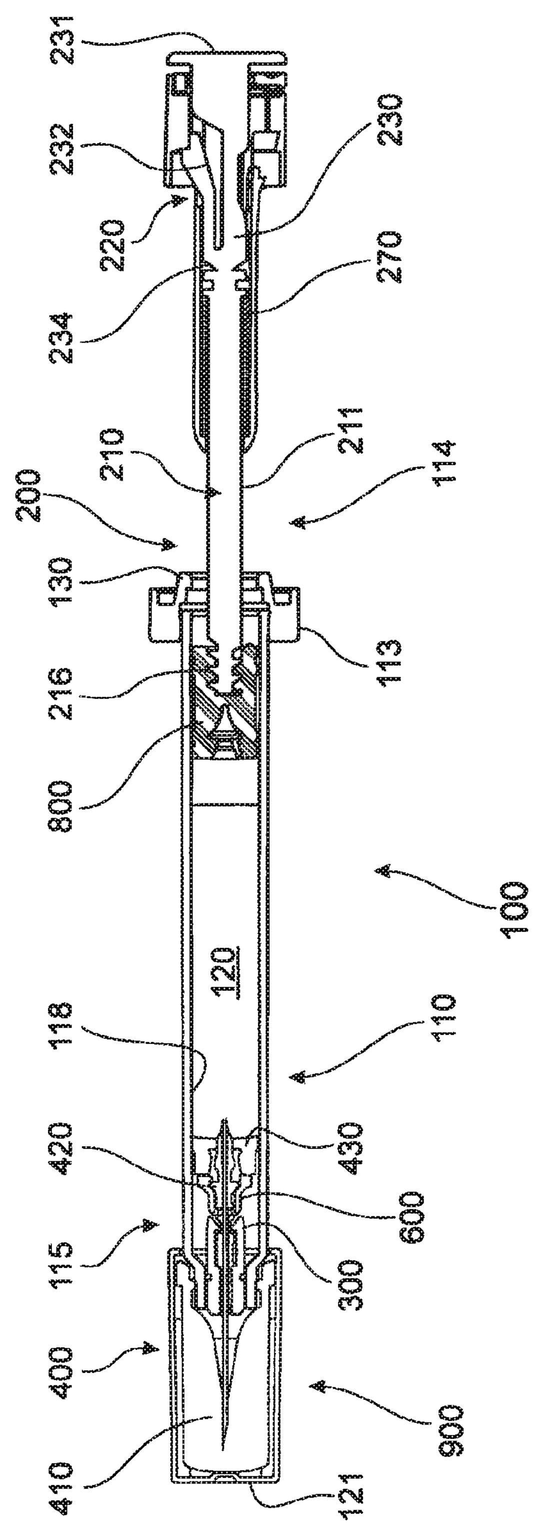
FIG. 1 is a sectional view of an embodiment of a retractable syringe.

Referring to FIG. 1, an embodiment of retractable syringe 100 comprises barrel 110 having plunger end 114 and needle end 115. Barrel 110 is preferably formed of glass. At plunger end 114 is located collar 113 having a releasing member in the form of release ring 130. Collar 113 may be mounted, glued, fitted or integrally formed with barrel 110. In embodiments where barrel 110 is formed of glass, suitably collar 113 is glued or otherwise adhered to barrel 110. In embodiments where barrel 110 is formed of plastic, collar 113 is preferably formed integrally with barrel 110 (e.g by moulding). Release ring 130 may be mounted, adhered or otherwise fitted to barrel 110, or may be co-moulded with collar 113 and barrel 110.

At needle end 115 of barrel 110 is mounted needle assembly 900 comprising retractable needle 400 that comprises cannula 410 and needle body 420, needle seal 430, ejector 600 and retainer 300. Typically, syringe 100 is supplied with removable protective cover 121 over cannula 410.

Syringe 100 further comprises plunger 200 comprising plunger seal 800 mounted thereto. Barrel 110 further comprises inside wall 118 which, together with needle seal 430 and plunger seal 800 define fluid space 120 inside barrel 110. In a preferred embodiment, fluid space 120 is prefilled with fluid contents to be delivered by retractable syringe 100.

Typically, barrel 110 is formed of glass. Preferably, retainer 300 is glued or otherwise adhered to inside wall 118 of barrel 110. In use, plunger 200 is movable axially into fluid space 120 to facilitate delivery of fluid contents of retractable syringe 100.

Figure 2:
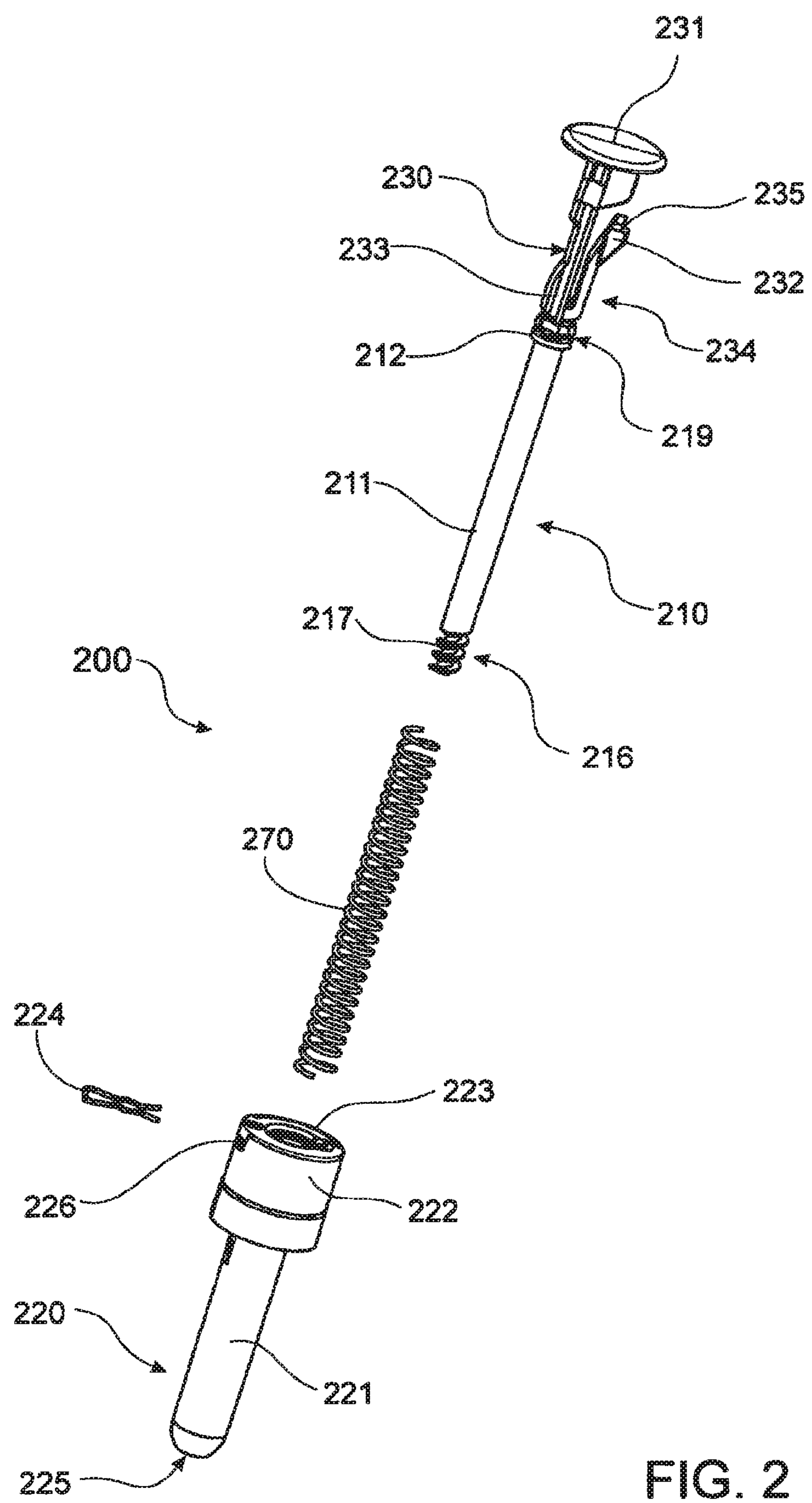
FIG. 2 is a sectional view of an embodiment of a plunger.
Figure 3:
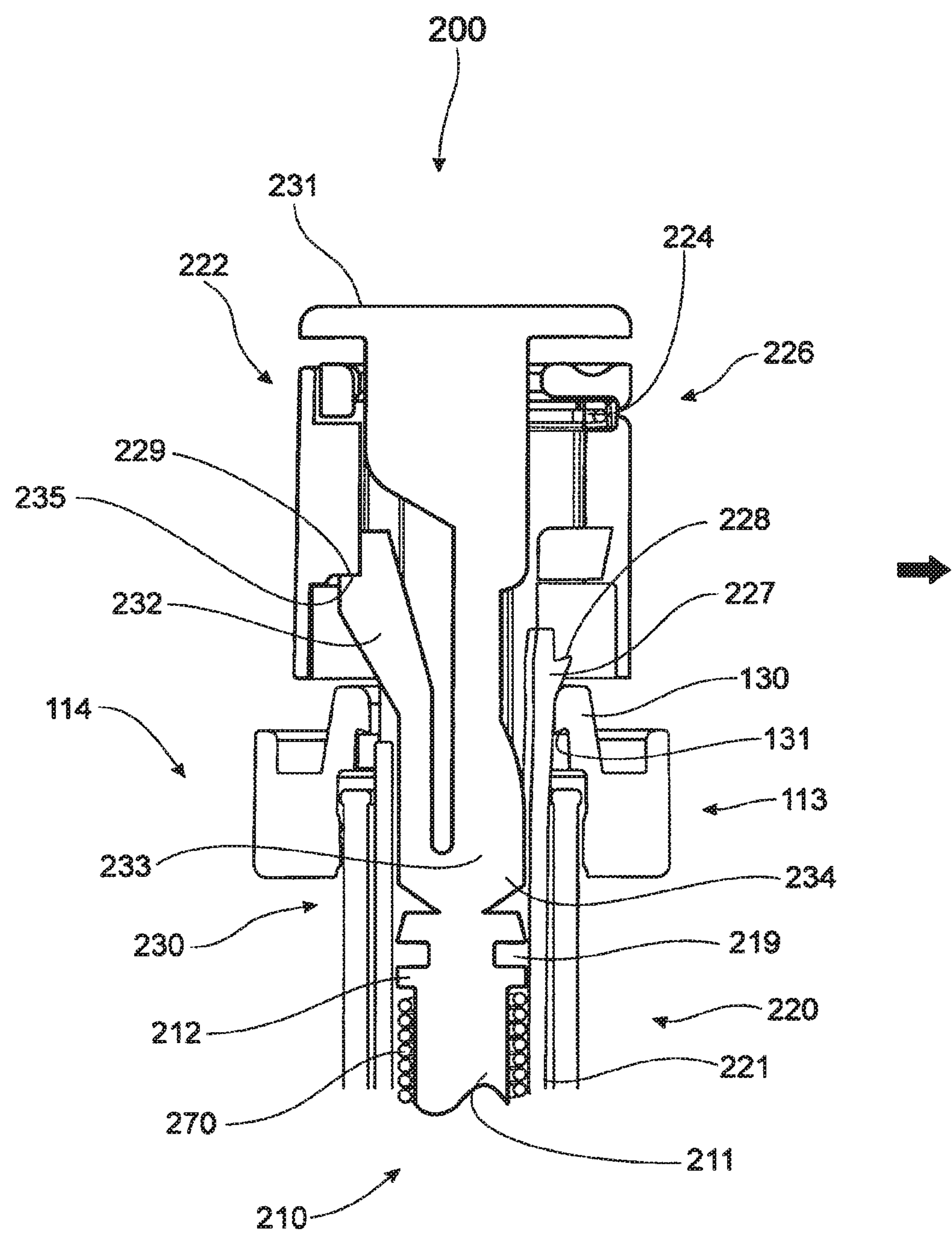
FIG. 3 is a sectional view of an embodiment of a plunger immediately before the end of injection of fluid contents of a syringe.
Figure 4:
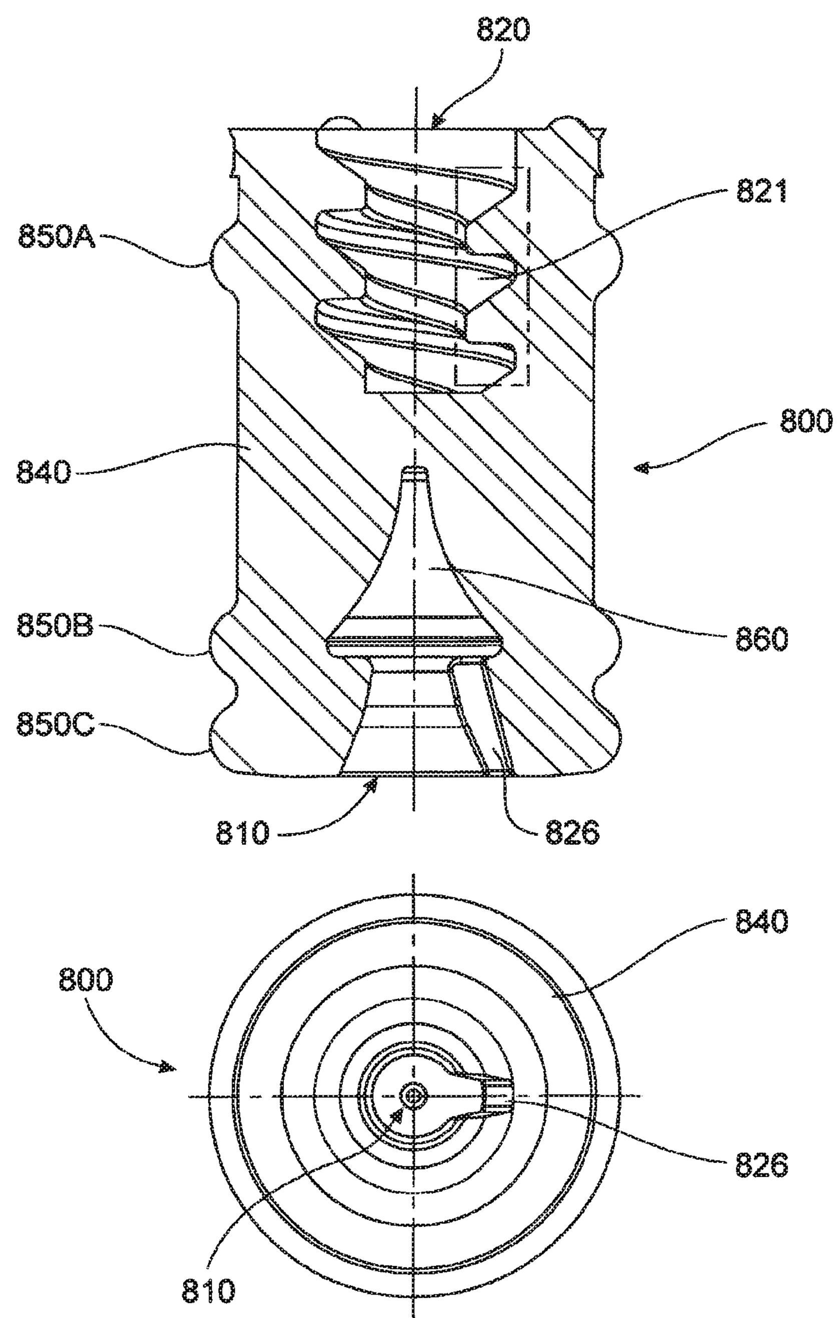
FIG. 4 is a sectional view and a bottom view of an embodiment of a plunger seal.

Referring particularly to FIG. 2, FIG. 3 and FIG. 4, plunger 200 comprises plunger member 210 comprising shaft 211, annular ledge 212 and seal-engaging member 216, which in this embodiment is screw threaded projection 217, which engages complementary, screw-threaded recess 820 of plunger seal 800 (see FIG. 4). In an alternative embodiment, seal engaging member 216 may be in the form of a snap lock projection that engages a complementary recess in plunger seal 800. In either case, the male-female connection between plunger member 210 and plunger seal 800 may readily be reversed so that the plunger member 210 has the female member and the plunger seal 800 has the male member.

Plunger member 210 further comprises locking groove 219, the function of which will be described in more detail hereinafter.

Plunger 200 further comprises plunger outer 220 having elongate body 221 with base 225 and head 222 in which is fitted cap 223. A first locking member comprises lock spring 224 mounted through slot 226 extending through head 222 and cap 223 to thereby assist assembly of plunger 200. Typically, lock spring 224 is an "R-shape" clip of stainless steel construction. Lock spring 224 and locking groove 219 co-operate to lock plunger member 210 and plunger outer 220 together at the end of retraction, as will be described in more detail hereinafter with reference to FIG. 12. Lock spring 224 preferably provides up to 100 Newton lockout resistance, which is a level of resistance desirable for syringe 100.

Elongate body 221 further comprises a second locking member comprising locking finger 227 which has abutment 228. Engagement between locking finger 227 and release ring 130 of collar 113 will also be described in more detail hereinafter with reference to FIG. 12.

Releasably, frangibly connected with plunger member 210 is control rod 230 comprising button 231, arm 232 and shaft 233. Plunger 200 further comprises compressed spring 270 which is mounted between plunger member 210 and plunger outer 220, held in an initially compressed state between annular ledge 212 of plunger member 210 and base 225 of plunger outer 220. Button 231 may have a textured surface to improve feel and grip for a user.

As best shown in FIG. 3, control rod 230 is releasably coupled to plunger member 210 by way of shaft 233 which is releasably connected to plunger member 210 by frangible junction 234. Control rod 230 also releasably engages plunger outer 220 to thereby retain spring 270 in an initially compressed state held between annular ledge 212 of plunger member 210 and base 225 of plunger outer 220. Initially, ledge 235 of arm 232 abuts rim 229 of head 222 of plunger outer 220 to thereby retain control rod 230 and prevent axial movement of control rod 230 relative to plunger outer 220. However, arm 232 of control rod 230 is resiliently flexible and movable in the direction of the solid arrow shown in FIG. 3, which will allow disengagement of control rod 230 from plunger outer 220 to facilitate decompression of spring 270, as will be described in detail hereinafter.

Figure 9:
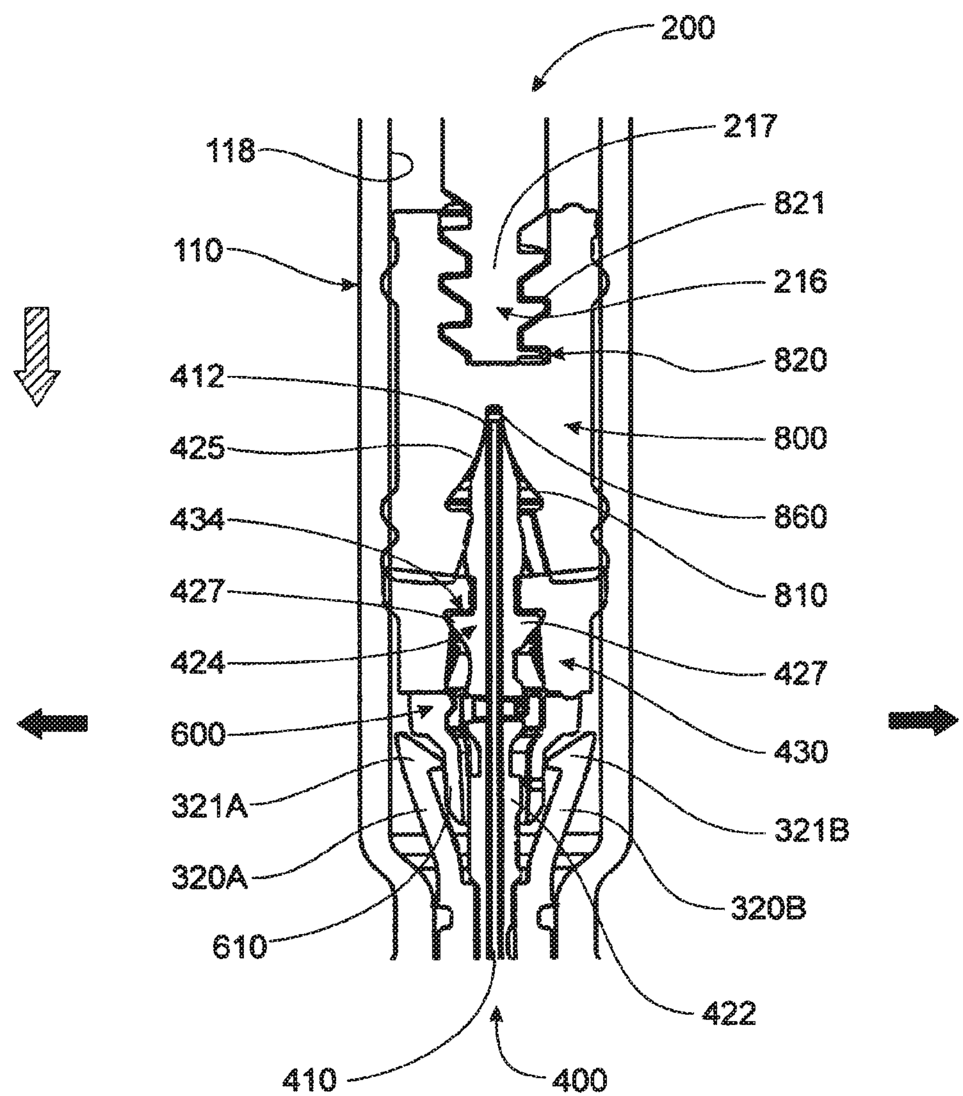
FIG. 9 is a sectional view of an embodiment of a needle assembly immediately before retraction of a retractable needle.

Referring particularly to FIG. 4, plunger seal 800 is of unitary construction and comprises seal body 840 and sealing ribs 850A, 850B, 850C that effect a fluid-tight seal between plunger 200 and inside wall 118 of barrel 110. Recess 820 of plunger seal 800 engages complementary seal-engaging member 216 of plunger member 210 (see FIG. 9). In this embodiment, recess 820 comprises a female screw thread 821 that engages male screw threaded projection 217 of plunger member. Plunger seal 800 further comprises needle engaging member in the form of recessed seat 810 that can receive segment 425 of retractable needle body 420. Plunger seal 800 also comprises recess 860 that receives fluid end 412 of cannula 410 towards the end of plunger 200 depression, prior to retraction of retractable needle 400, as will be described hereinafter. In addition, recess 860 of plunger seal 800 comprises fluid conduit 826.

Figure 5:
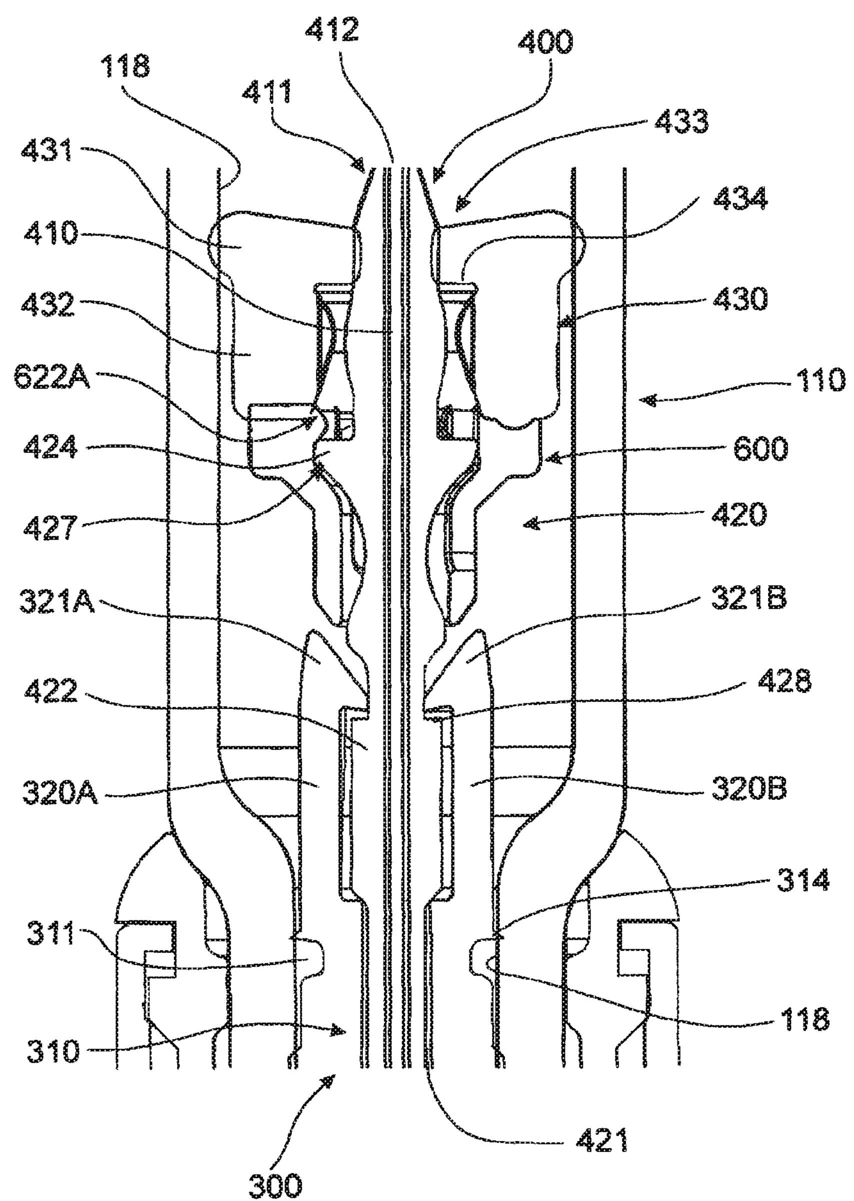
FIG. 5 is a sectional view of an embodiment of a needle assembly.
Figure 6:
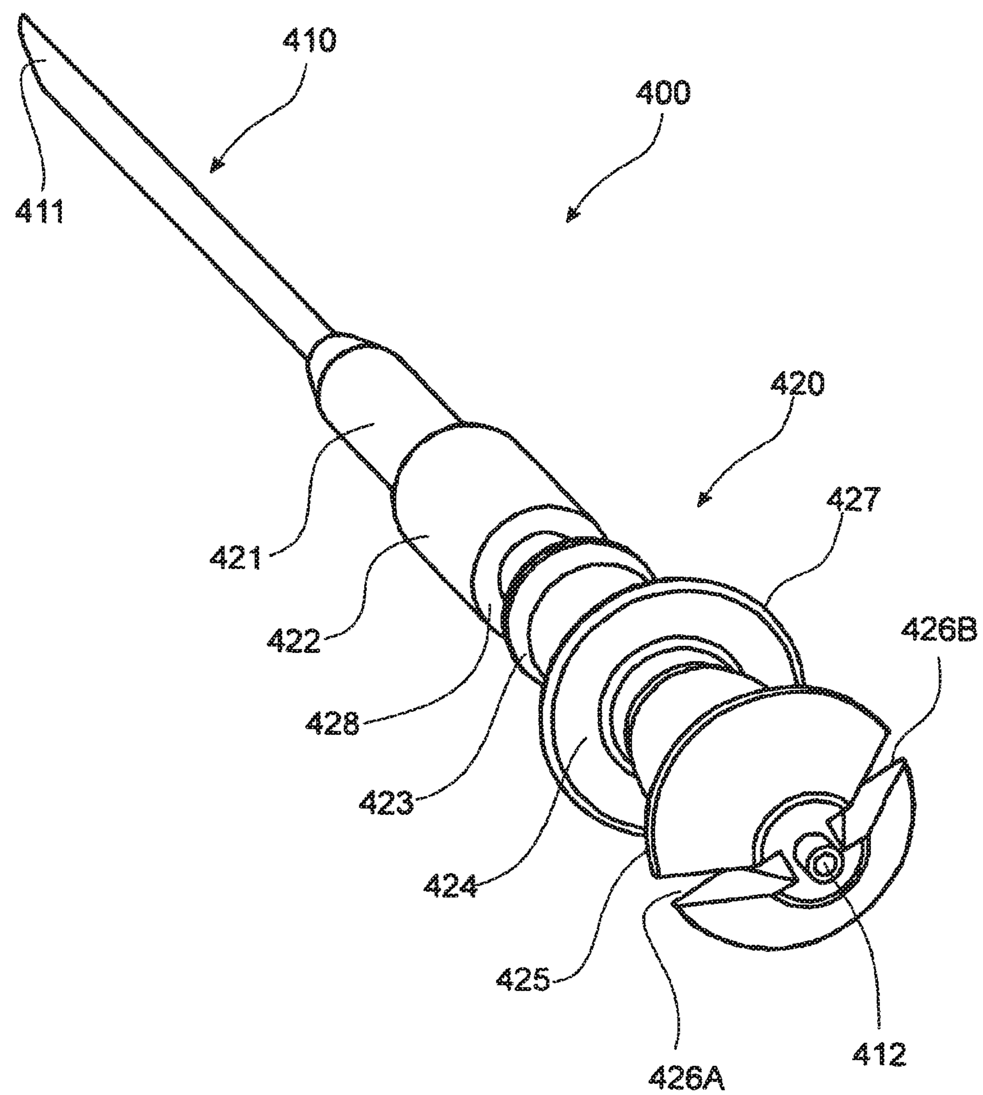
FIG. 6 is a perspective view of an embodiment of a retractable needle.
Figure 7:
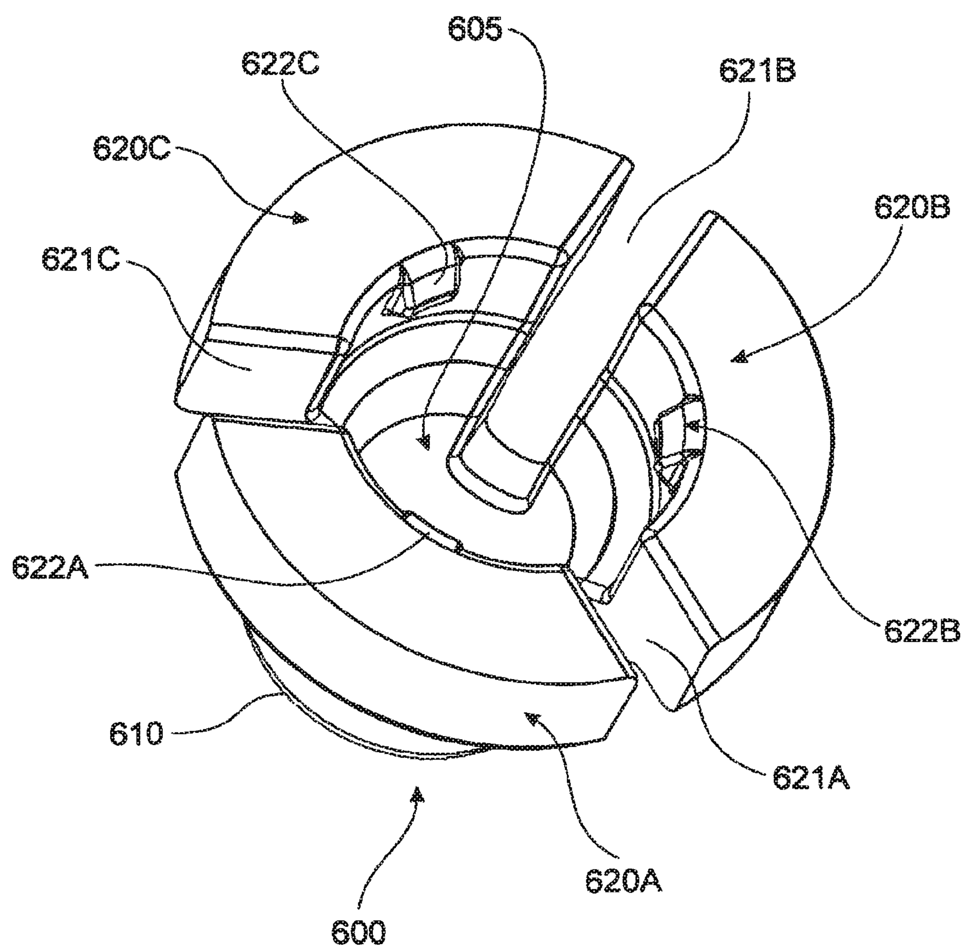
FIG. 7 is a perspective view of an embodiment of an ejector.

Needle assembly 900 is shown in more detail in FIG. 5, which comprises retractable needle 400, retainer 300, needle seal 430 and ejector 600. These components are individually described with reference to FIGS. 6, 7 and 8 respectively. Referring to FIG. 6, retractable needle 400 comprises cannula 410 having delivery end 411 and fluid end 412. Retractable needle 400 further comprises needle body 420 which comprises respective body segments 421, 422, 423, 424 and 425. Body segment 425 comprises fluid channels 426A, 426B. Needle body segment 424 comprises shoulder 427 and needle body segment 422 comprises shoulder 428. In FIG. 7, ejector 600 comprises ejector ring 610, bore 605 and respective base segments 620A, B, C separated by slots 621A, B, C. Base segments 620A, B, C respectively comprise tabs 622A, B, C which as shown in FIG. 5, engage shoulder 427 of body segment 424 of needle body 420.

Figure 8:
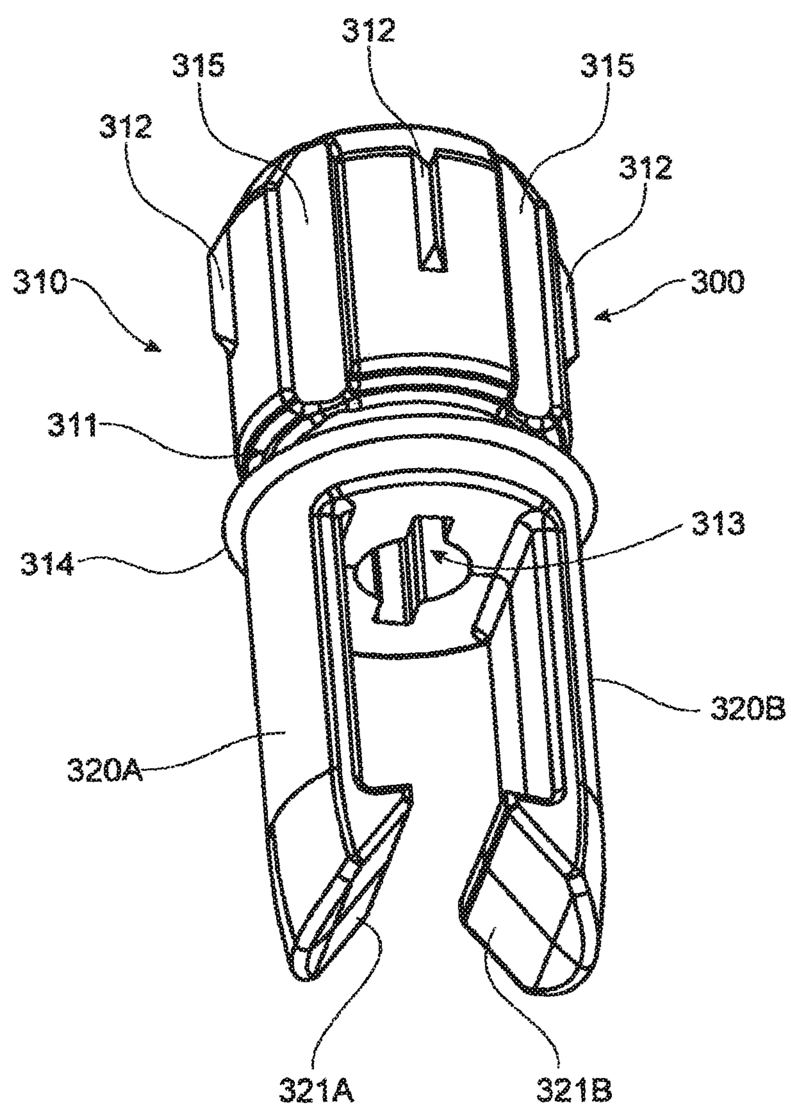
FIG. 8 is a perspective view of an embodiment of a retainer.

Referring to FIG. 8, retainer 300 comprises body 310 comprising circumferential groove 311, centering bosses 312, central aperture 313, rim 314 and guide channels 315, and further comprises arms 320A, 320B, respectively comprising hook-ends 321A, 321B. Circumferential groove 311 and guide channels 315 create zones which facilitate or guide the flow of glue or adhesive for adhering retainer 300 to inside wall 118 of barrel 110. Centering bosses 312 have been included to overcome the potential problem of centering retainer 300 in barrel 110 by providing a self-centering mechanism that simplifies centering of these components in high speed assembly and gluing machines, as would typically be used for the assembly of syringe 100. Centering bosses 312 allow contact between retainer 300 and barrel 110 at four separate points, with components produced for all extremes of tolerance. The tolerance variations between barrel 110 and retainer 300 are absorbed by the crushing of centering bosses 312. In the absence of these structures, a gap would be required between these components to allow for assembly at all tolerance extremes, which would require automated assembly machines to have a system for centering the parts prior to gluing. Alternatively, centering would have to be performed by a mechanism external to, or otherwise separate from, the assembly machines. This would not be practical for high speed assembly.

Referring again to FIG. 5, needle seal 430 comprises sealing base 431 which seals against inside wall 118 of barrel 110 to prevent inadvertent leakage of fluid contents, body 432 comprising internal bore 433 and ledge 434.

The sequence of events whereby retractable needle 400 is disengaged from retainer 300 to facilitate retraction of retractable needle 400 is as follows.

Typically, syringe 100 is provided prefilled with fluid contents for delivery. Therefore, plunger 200 is provided in an initial position ready for depression to deliver the fluid contents of the syringe 100. During delivery of fluid contents, plunger 200 moves axially through barrel 110 in the direction of the hatched arrow in FIG. 9. Plunger seal 800 bears against needle seal 430, which in turn bears against ejector 600 thereby pushing tabs 622A, B, C of ejector 600 out of engagement with needle body 420. In order to provide an acceptable or desired level of retraction activation force, tabs 622A, B, C allow for tuning of the force to disengage ejector 600 from needle body 420 by adjusting the height of the tabs 622 until the push force required on needle seal 430 to force ejector 600 out of engagement with shoulder 427 of needle body 420 is at a level that is acceptable for use of syringe 100. The design of tabs 622A, B, C provides for simple machining of the injection-moulding tool to provide the optimum engagement fit to provide acceptable disengagement.

Ledge 434 of needle seal 430 now rests on shoulder 427 of needle body segment 424. This facilitates moving needle seal 430 back up barrel with the needle 400 on retraction (and serves as a stop for forward travel), Further to this, ejector ring 610 moves hook-ends 321A, B of arms 320A, B radially outwardly in the direction of the solid arrows in FIG. 9, thereby disengaging segment 422 of needle body 420 from retainer 300 to release retractable needle 400 for subsequent retraction. At this point, recessed seat 810 of plunger seal 800 has engaged segment 425 of retractable needle body 420 and recess 860 has received fluid end 412 of cannula 410. This effectively couples retractable needle 400 to plunger member 210. Although not visible in FIG. 9, fluid channels 426A, 426B in segment 425 and fluid conduit 826 in recessed seat 810 in plunger seal 800 assist in channeling residual fluid from within recessed seat 810 into fluid end 412 of cannula 410. This minimizes "dead volume" (i.e a volume of undeliverable, hence wasted, fluid contents) and reduces the possibility of a "hydraulic lock", to thereby improve the efficiency with which fluid contents of syringe 100 are delivered.

Figure 10:
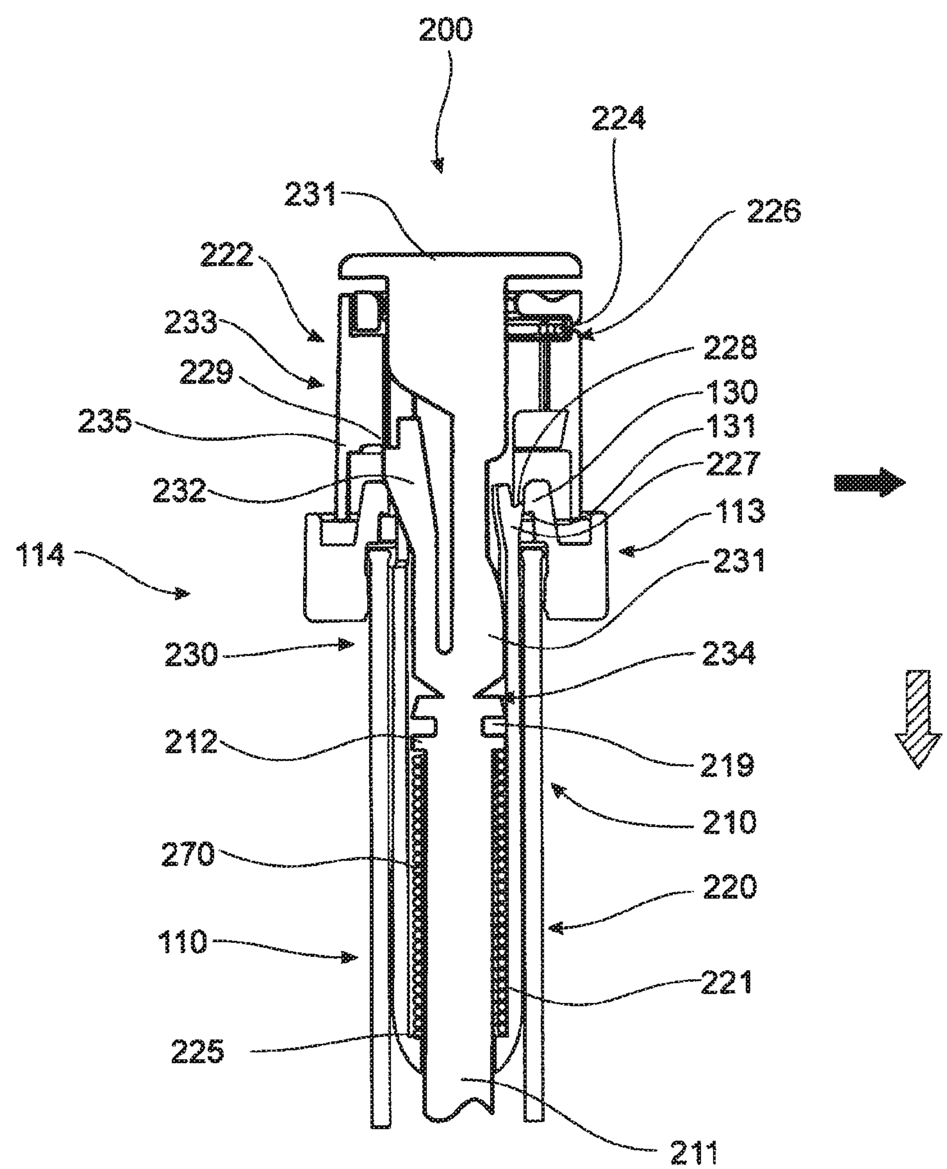
FIG. 10 is a sectional view of an embodiment of a plunger immediately before retraction.

Referring to FIG. 10, plunger 200 moves axially in the direction of the hatched vertical arrow until the end of injection of fluid contents, at which time abutment 228 of locking finger 227 of plunger outer 220 engages underside 131 of release ring 130 to thereby prevent movement of plunger outer 220 out of barrel 110.

Figure 11:
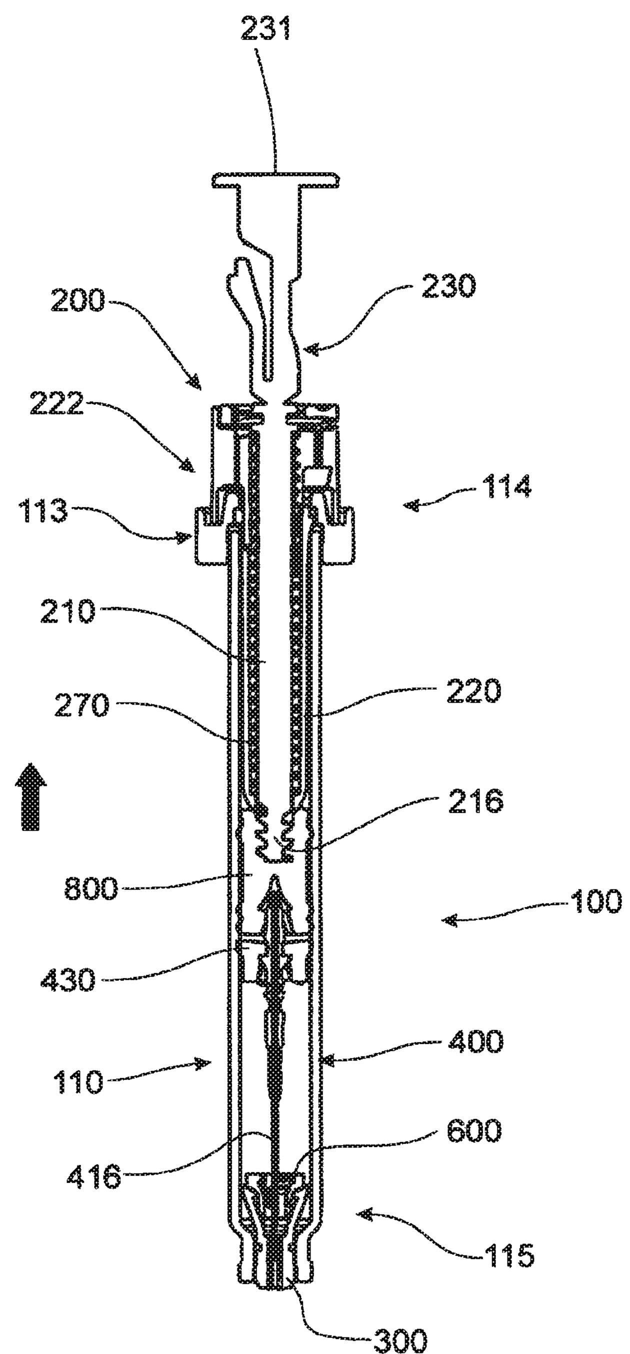
FIG. 11 is a sectional view of an embodiment of a syringe during retraction of a plunger and retractable needle engaged therewith.

In order for retractable needle 400 to retract at the end of delivery of fluid contents, compressed spring 270 must decompress, which is facilitated by plunger member 210 disengaging from plunger outer 220. Again referring to FIG. 10, arm 232 of control rod 230 bears against release ring 130 of collar 113 at plunger end 114 of barrel 110. Release ring 130 forces arm 232 to move radially inwardly n the direction of the horizontal solid arrow and out of engagement with rim 229 of cap member 223 of plunger outer 220 in FIG. 10. This disengagement allows compressed spring 270 to decompress and push against ledge 212 of plunger member 210 to thereby retract plunger member 210 with control rod 230 coupled thereto, as shown in FIG. 11. This disengagement may also be accompanied by an audible and/or tactile signal (e.g. a "click") which indicates to the user that retraction will occur. Retractable needle 400 is coupled to plunger seal 800 and so retracts with plunger member 210 in the direction of the arrow in FIG. 11 inside barrel 110, thereby being completely enveloped by, and contained within, barrel 110. While retraction of needle 400 is "automatically" driven by decompression of spring 270, the rate of retraction can be controlled by a user relaxing pressure (such as by way of thumb pressure) against button 231 of control rod 230.

Figure 12:
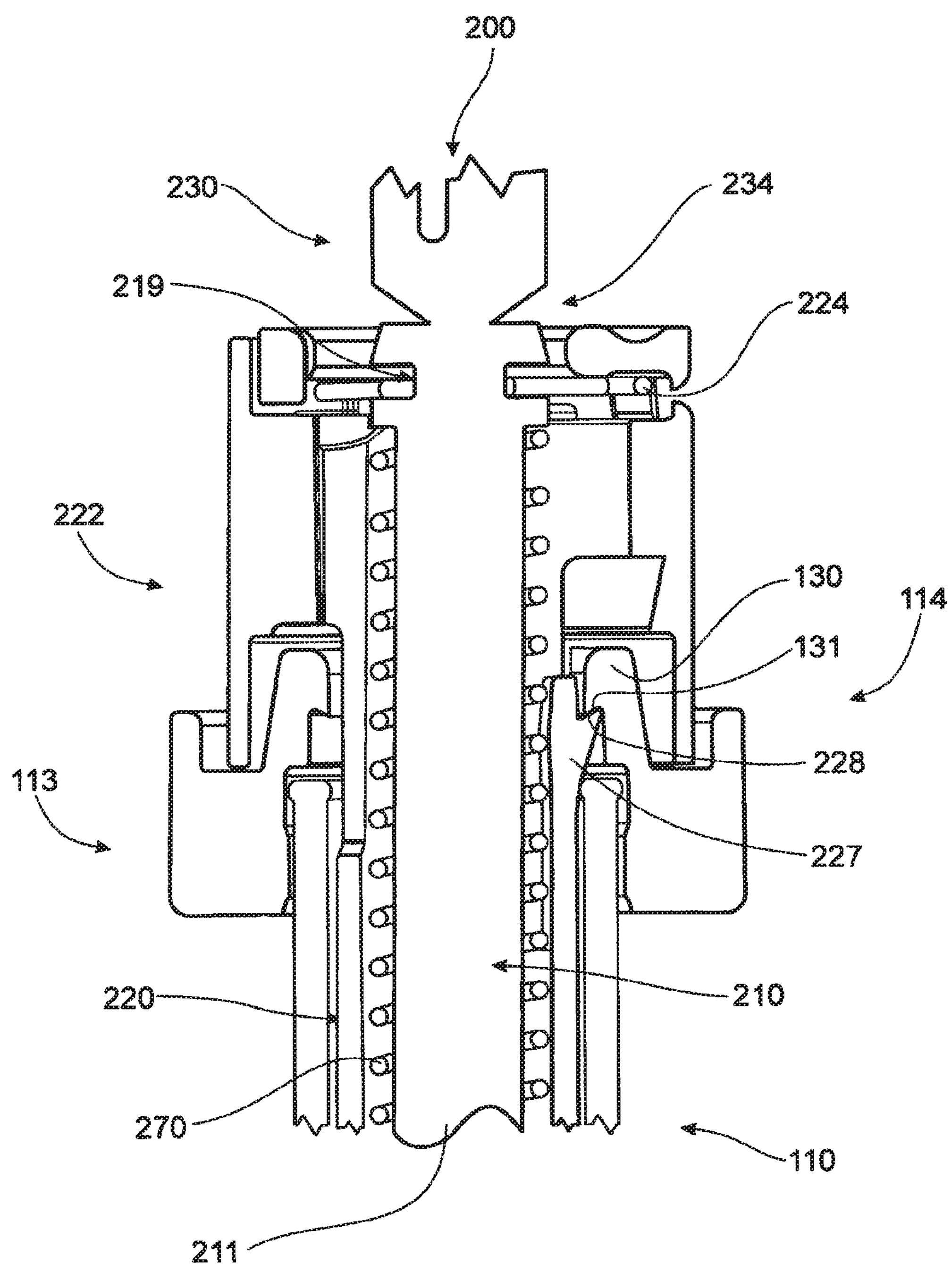
FIG. 12 is a sectional view of a lock formed between a barrel collar and a plunger outer after plunger retraction.

Referring to FIG. 12, at the end of retraction of plunger member 210, further movement of plunger member 210 relative to plunger outer 220 and/or barrel 110 is prevented by lock spring 224 "snap locking" around locking groove 219 in plunger member 210. The locking of plunger member 210 at the end of retraction prevents inadvertent removal of plunger member 210 from plunger outer 220 and also prevents inadvertent depression of plunger member 210, both of which would expose delivery end 411 of the cannula, and thereby expose the user to a potential needle stick injury.

At the end of retraction of plunger member 210 and retractable needle 400, control rod 230 can be broken from plunger member 210 at frangible junction 234 and manually removed from retractable syringe 100 and discarded as "clean" waste so that there is little if any plunger 220 protruding externally from barrel 110 with which to attempt to force plunger 200 back into barrel 110 and attempt to re-engage the needle (not shown).

In light of the foregoing it will be appreciated that the present invention provides a relatively simple, robust and inexpensive syringe that is automatically disabled with little or no assistance from the user to thereby prevent, or at least minimize the likelihood of, re-use of the syringe and/or needlestick injury by a used syringe.

More particularly, dual locking systems are provided whereby the plunger outer is locked to the barrel and the plunger member is locked to the plunger outer to thereby prevent removal and/or further movement of the plunger. Another particular advantage is provided by the lock spring which can resist up to 100 Newtons force to prevent or impede further movement of the plunger member after retraction. By providing dual locking systems, inadvertent failure of one or the other locking systems, or overcoming one or the other locking systems through tampering by an illicit user, does not result in the complete failure of plunger lockout.

It will also be appreciated that the fluid conduits in the retractable needle body and in the plunger seal provide more efficient delivery of fluid contents timed to occur just before retraction of the needle. In cases where the fluid contents are an expensive drug or other compound, on a mass produced scale this improved efficiency can result in considerable cost savings. Furthermore, the retractable syringe retainer provides a convenient "self-centering" system for mounting into the barrel which greatly assists high speed syringe assembly. The guide channels of the retainer also assist rapid, automated adhesion of the retainer in the barrel during syringe assembly.

Another advantage is provided by the ejector tabs described herein that provide an acceptable or desired level of retraction activation force. Adjustment of tab height allows for tuning of the force to disengage the ejector from the retractable needle body, and hence the "push" force required to force the ejector out of engagement with the retractable needle body.

While example embodiments have been particularly shown and described, it will be understood by those skilled in the art that various changes in form and details may be made therein without departing from the scope of the embodiments encompassed by the appended claims.

What is claimed is:

1. A needle retainer for a retractable needle, the needle retainer comprising a unitary structure having a body portion and an arm portion, the body portion including protruding centering bosses, a circumferential groove, and recessed guide channels that create zones which facilitate or guide a flow of glue or adhesive for adhering the needle retainer to a barrel, the circumferential groove disposed between the body portion and the arm portion, the arm portion comprising a plurality of arms configured to releasably engage the retractable needle.

2. The needle retainer of claim 1, wherein the centering bosses are circumferentially spaced apart on the body portion of the needle retainer.

3. The needle retainer of claim 1, wherein the body portion comprises a central aperture configured to receive the retractable needle.

4. The needle retainer of claim 3, wherein each of the plurality of arms comprises a barbed end for releasably engaging the retractable needle.

5. A needle assembly comprising:

a retractable needle that comprises a cannula and a needle body comprising one or more fluid channels that in use direct fluid to the cannula; and a needle retainer comprising a unitary structure having a body portion and an arm portion, the body portion including protruding centering bosses, a circumferential groove, and recessed guide channels that create zones which facilitate or guide a flow of glue or adhesive for adhering the needle retainer to a barrel, the circumferential groove disposed between the body portion and the arm portion, the arm portion comprising a plurality of arms configured to releasably engage the retractable needle, the retractable needle disposed within a central aperture of the needle retainer and releasably coupled to the needle retainer.

6. The needle assembly of claim 5, wherein the one or more fluid channels co-operate with one or more fluid conduits of a plunger seal to direct the fluid to said cannula.

7. The needle assembly of claim 5, wherein the needle body is engageable by a needle-engaging member of a plunger seal to facilitate retraction of said retractable needle.

8. The needle assembly of claim 5, wherein each of the plurality of arms comprises a barbed end releasably coupled to the needle body.

9. The needle assembly of claim 5, further comprising an ejector.

10. The needle assembly of claim 9, wherein the ejector facilitates release of the retractable needle from the needle retainer to allow retraction of the retractable needle when engaged by a plunger.

11. The needle assembly of claim 9, wherein the ejector comprises a plurality of tabs that releasably engage the retractable needle.

12. The needle assembly of claim 11, wherein the tabs provide a retraction activation force for disengaging the retractable needle.

13. The needle assembly of claim 5, further comprising a needle seal.

14. A retractable syringe comprising:

a barrel;

a plunger; and a needle assembly comprising:

a retractable needle that comprises a cannula and a needle body comprising one or more fluid channels that in use direct fluid to said cannula; and a needle retainer comprising a unitary structure having a body portion and an arm portion, the body portion including protruding centering bosses, a circumferential groove, and recessed guide channels that create zones which facilitate or guide a flow of glue or adhesive for adhering the needle retainer to a barrel, the circumferential groove disposed between the body portion and the arm portion, the arm portion comprising a plurality of arms configured to releasably engage the retractable needle, the retractable needle disposed within a central aperture of the needle retainer and releasably coupled to the needle retainer.

15. The retractable syringe of claim 14, wherein the plunger comprises a plunger seal, and wherein the one or more fluid channels co-operate with one or more fluid conduits of the plunger seal to direct the fluid to the cannula.

16. The retractable syringe of claim 14, wherein each of the plurality of arms comprises a barbed end releasably coupled to the needle body.

17. The retractable syringe of claim 14, further comprising an ejector that facilitates release of the retractable needle from the needle retainer to allow retraction of the retractable needle when engaged by the plunger.

18. The retractable syringe of claim 17, wherein the ejector comprises a plurality of tabs that releasably engage the retractable needle.

* * * * *